US012667583B2

(12) United States Patent
Chang et al.

(10) Patent No.: US 12,667,583 B2
(45) Date of Patent: Jun. 30, 2026

(54) METHOD FOR PREVENTING OR TREATING A CORNAVIRUS INFECTIOUS DISEASE

(71) Applicant: HENAN GENUINE BIOTECH CO., LTD., Pingdingshan (CN)

(72) Inventors: Junbiao Chang, Pingdingshan (CN); Jinfa Du, Pingdingshan (CN); Jiandong Jiang, Pingdingshan (CN); Yuhuan Li, Pingdingshan (CN)

(73) Assignee: HENAN GENUINE BIOTECH CO., LTD., Pingdingshan (CN)

( * ) Notice: Subject to any disclaimer, the term of this patent is extended or adjusted under 35 U.S.C. 154(b) by 964 days.

(21) Appl. No.: 17/905,142

(22) PCT Filed: Feb. 20, 2021

(86) PCT No.: PCT/CN2021/077010

§ 371 (c)(1),
(2) Date: Aug. 26, 2022

(87) PCT Pub. No.: WO2021/169861

PCT Pub. Date: Sep. 2, 2021

(65) Prior Publication Data

US 2023/0277576 A1 Sep. 7, 2023

(30) Foreign Application Priority Data

Feb. 27, 2020 (CN) ........................ 202010125799.2

(51) Int. Cl.

| | |
|---|---|
| ***A61K 31/706*** | (2006.01) |
| ***A61K 31/7068*** | (2006.01) |
| ***A61K 31/7072*** | (2006.01) |
| ***A61K 31/7076*** | (2006.01) |
| ***A61P 31/14*** | (2006.01) |

(52) U.S. Cl.

CPC ........ *A61K 31/7068* (2013.01); *A61K 31/706* (2013.01); *A61K 31/7072* (2013.01); *A61K 31/7076* (2013.01); *A61P 31/14* (2018.01)

(58) Field of Classification Search

CPC .............. A31K 31/706; A31K 31/7076; A31K 31/7072

USPC ........................................................... 514/49

See application file for complete search history.

(56) References Cited

U.S. PATENT DOCUMENTS

| | | | |
|---|---|---|---|
| 10,434,116 B2 * | 10/2019 | Frieman | A61K 38/215 |
| 2004/0259934 A1 | 12/2004 | Olsen et al. | |
| 2007/0042988 A1 | 2/2007 | Klumpp et al. | |
| 2010/0234584 A1 | 9/2010 | Chang | |
| 2012/0070415 A1 | 3/2012 | Beigelman et al. | |
| 2013/0165400 A1 | 6/2013 | Beigelman et al. | |

FOREIGN PATENT DOCUMENTS

| | | |
|---|---|---|
| WO | 03018030 A1 | 3/2003 |
| WO | 2005020885 A1 | 3/2005 |
| WO | 2009067409 A1 | 5/2009 |
| WO | 2020007070 A1 | 1/2020 |

OTHER PUBLICATIONS

Ju, Jingyue, et al; Nucleotide Analogues as Inhibitors of Viral Polymerases; BioRxiv, Jan. 31, 2020; pp. 1-8.

Chen, Yu Wai, et al; Prediction of the SARS-CoV-2 (2019-nCoV) 3C-like protease (3CLpro) structure: virtual screening reveals velpatasvir, ledipasvir, and other drug repurposing candidates; F1000Research; 2020, vol. 9; No. 129; pp. 1-19.

Ju, Jingyue, et al; Nucleotide analogues as inhibitors of SARS-CoV Polymerase; Pharmacology Research & Perspectives; Sep. 21, 2020; pp. 1-9.

Chien, Minchen, et al; Nucleotide Analogues as Inhibitors of SARS-CoV-2 Polymerase; BioRxiv, Mar. 20, 2020; pp. 1-7.

Zhang, Xue Wu, et al; Generation of predictive pharmacophore model for SARS-coronavirus main proteinase; European Journal of Medicinal Chemistry; 402 (2005); Nov. 5, 2004; pp. 57-62.

Azzi, Arezki, et al; Human SARS-Coronavirus RNA-Dependent RNA Polymerase: Activity Determinants and Nucleoside Analogue Inhibitors; Proteins: Structure, Function, and Bioinformatics; vol. 57; Jun. 11, 2004; pp. 12-14.

Barnard, Dale L., et al; Inhibition of severe acute respiratory syndrome-associated coronavirus (SARSCoV) by calpain inhibitorsand β-D-N4-hydroxycytidine; Antiviral Chemistry & Chemotherapy; vol. 15, Dec. 31, 2004, pp. 15-22.

International Search Report issued in International Application No. PCT/CN2021/077010; mailed May 21, 2021; 11 pgs.

Cinatl et al., "Glycyrrhizin, an active component of liquorice roots, and replication of SARS-associated coronavirus", The Lancet, vol. 361, Jun. 14, 2003; 2 pgs.

Dyall et al., "Repurposing of Clinically Developed Drugs for Treatment of Middle East Respiratory Syndrome Coronavirus Infection", American Society for Microbiology, May 19, 2014; 9 pgs.

Examination Report in Corresponding New Zealand Application No. 791549, dated May 7, 2025; 5 pgs.

Examination Report in Corresponding Vietnamese Application No. 1-2022-05401, dated Jan. 17, 2025; 6 pgs.

Examination Report No. 1 in Corresponding Australian Application No. 2021228008, dated Sep. 8, 2023; 5 pgs.

Examination Report No. 2 in Corresponding Australian Application No. 2021228008, dated Apr. 5, 2025; 4 pgs.

(Continued)

*Primary Examiner* — Traviss C Mcintosh, III

(74) *Attorney, Agent, or Firm* — HAUPTMAN HAM, LLP

(57) ABSTRACT

The present invention relates to a method for preventing or treating a coronavirus infectious disease, comprising administering to a patient in need thereof a therapeutically or prophylactically effective amount of a compound represented by formula (I) or pharmaceutically acceptable salts thereof. The compound represented by formula (I) is used for treating patients with novel coronavirus pneumonia, and shows obvious advantages in all of the clearance rate by viral nucleic acid test, the course of clearance, and the cure and discharge time.

10 Claims, No Drawings

Specification includes a Sequence Listing.

(56) References Cited

OTHER PUBLICATIONS

Examination Report No. 3 in Corresponding Australian Application No. 2021228008, dated Jun. 7, 2025; 3 pgs.
Extended Search Report in Corresponding European Application No. 21760199.6, dated Feb. 20, 2024; 12 pgs.
Falcone et al., "Can Adenosine Fight COVID-19 Acute Respiratory Distress Syndrome?", Journal of Clinical Medicine, Sep. 21, 2020; 16 pgs.
First Examination Report in Corresponding Moroccan Application No. 57574, dated Nov. 3, 2023; 4 pgs.
First Office Action in Corresponding Eurasian Application No. 202292091/28, dated Oct. 31, 2023; 6 pgs.
Jang et al., "Comparison of Antiviral Activity of Gemcitabine with 21-Fluoro-2' -Deoxycytidine and Combination Therapy with Remdesivir against SARS-CoV-2", International Journal of Molecular Sciences, Feb. 4, 2021; 15 pgs.
Kuzikov et al., "Identification of inhibitors of SARS-CoV-2 3CL-Pro enzymatic activity using a small molecule In-vitro repurposing screen", bioAxiv, Dec. 16, 2020; 29 pgs.
Li et al., "Comparative efficacy and safety of current drugs against COVID-19: A systematic review and network meta-analysis", Nov. 18, 2020; 25 pgs.
Mehellou et al., "Phosphoramidates of 2'-P-o-arabinouridine (AraU) as phosphate prodrugs; design, synthesis, in vitro activity and metabolism", Bioorganic & Medicinal Chemistry, Mar. 1, 2010; 8 pgs.
Notice of Final Rejection in Corresponding Korean Application No. 10-2022-7030688, dated May 19, 2025; 8 pgs.
Notice of Reasons for Refusal in Corresponding Japanese Patent Application No. 2022-551819, dated Aug. 3, 2023; 9 pgs.
Notification of Defects in Corresponding Israel Patent Application No. 295840, dated Jun. 18, 2025; 8 pgs.
Office Action in Corresponding Canadian Application No. 3,167,927, dated Oct. 16, 2023; 4 pgs.
Office Action in Corresponding Thai Application No. 2201005342, dated Aug. 29, 2025; 10 pgs.
Ren et al., "A Randomized, Open-Label, Controlled Clinical Trial of Azvudine Tablets in the Treatment of Mild and Common COVID-19, a Pilot Study", Advanced Science, Aug. 13, 2020; 10 pgs.
Request for the Submission of an Opinion in Corresponding Korean Application No. 10-2022-7030688, dated Sep. 6, 2024; 15 pgs.
Search Report and Written Opinion in Corresponding Singapore Application No. 11202252149V, dated May 19, 2025; 11 pgs.
Second Notice of Reasons for Refusal in Corresponding Japanese Patent Application No. 2022-551819, dated Jan. 5, 2024; 7 pgs.
Second Office Action in Corresponding Canadian Application No. 3,167,927, dated Aug. 9, 2024; 3 pgs.
Second Office Action in Corresponding Eurasian Application No. 202292091/28, dated Jun. 27, 2024; 3 pgs.
Second Office Action in Corresponding Moroccan Application No. 57574, dated May 30, 2024; 5 pgs.
Substantive Examination Report Stage I in Corresponding Indonesian Application No. P00202209466; 3 pgs.
Third Office Action in Corresponding Eurasian Application No. 202292091/28, dated Jan. 23, 2025; 3 pgs.
Yu et al., "Azvudine (FNC): a promising clinical candidate for COVID-19 treatment", Signal Transduction and Targeted Therapy, Oct. 10, 2020; 3 pgs.

* cited by examiner

METHOD FOR PREVENTING OR TREATING A CORNAVIRUS INFECTIOUS DISEASE

RELATED APPLICATIONS

The present application is a U.S. National Phase of International Application Number PCT/CN2021/077010, filed Feb. 20, 2021, and claims priority to Chinese Application Number 202010125799.2, filed Feb. 27, 2022.

INCORPORATION BY REFERENCE

The sequence listing provided in the file entitled SEQUENCE_LISTING_ST25_V2.txt, which is a text file that was created on Sep. 13, 2022, and which comprises 594 bytes, is hereby incorporated by reference in its entirety.

TECHNICAL FIELD

The present disclosure relates to novel antiviral use of nucleoside compounds.

BACKGROUND

Coronavirus (CoV), a class of enveloped positive single-stranded RNA viruses, spreads widely in humans, other mammals, and birds, and may cause respiratory diseases, intestinal diseases, liver diseases, nervous system diseases, and the like. Seven CoVs are now known to cause human diseases, four of which, i.e., CoV-229E, —OC43, -NL63, and —HKU1, are prevalent in population and usually cause symptoms of the common cold. However, the other three CoVs, i.e., SARS-CoV, MERS-CoV, and 2019-nCoV (or known as COVID-19), all have severe hazards of quick onset, strong infectivity, and a high fatality rate. It is therefore very urgent to rapidly develop direct-acting antiviral drugs for use in treatment of novel coronavirus infection.

SUMMARY

Compound 1, as an anti-AIDS drug, has passed the phase II clinical trials and showed good safety.

1

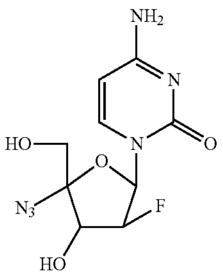

The inventors have determined the in vitro antiviral activity of Compound 1 in MRC-5 cells infected with the novel coronaviruses. The results show that Compound 1 has only a weak inhibitory activity against the novel coronaviruses (EC50 is 25 μM).

However, when using the compound of formula (1) to directly conduct clinical trials for research, the inventors have surprisingly found that compared with the conventional treatment as a control, treating patients with novel coronavirus pneumonia with the compound of formula (1) shows obvious advantages in the clearance rate by viral nucleic acid test, the course of clearance, and the cure and discharge time. The inventors believe that Compound 1 does not show a significant inhibitory effect against the viruses, which may be because it cannot be effectively phosphorylated in vitro.

In view of the above, on one aspect, there is provided herein use of a compound represented by formula (I) or pharmaceutically acceptable salts thereof in the preparation of a medication for preventing or treating a coronavirus infectious disease, and on the other aspect, there is provided herein a method for preventing or treating a coronavirus infectious disease, comprising administering to a patient in need thereof a therapeutically or prophylactically effective amount of a compound represented by formula (I) or pharmaceutically acceptable salts thereof, wherein the formula (I) has the following structure:

(I)

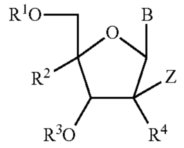

in the formula (I),

R1 is any group that enables an OR1 group to be metabolized in vivo to release a hydroxyl group, or to form an O-phosphate group; OR1 is preferably an ester group, R1 is preferably H, $R^5$—CO—, or

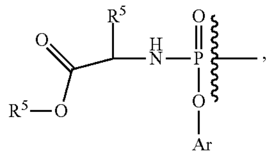

wherein Ar is phenyl and substituted phenyl, naphthyl and substituted naphthyl, and the substituents are selected from the group consisting of $C_{1-6}$ alkyl, F, Cl, Br, I, CN, $N_3$, OH, $NH_2$, $OR^5$, and $NHR^5$;

$R^2$ is selected from the group consisting of: H, azido, $C_1$-$C_6$ alkyl (e.g., methyl or ethyl), $C_1$-$C_6$ alkoxy (e.g., methoxy or ethoxy), $C_2$-$C_6$ alkynyl (e.g., ethynyl), $C_2$-$C_6$ alkenyl (e.g., ethenyl), or halo $C_1$-$C_6$ alkyl (e.g., 2-chloroethyl, 2-fluoroethyl, or trifluoroethyl);

$R^3$ is selected from the group consisting of H, optionally substituted R—CO—, optionally substituted R—O(C═O)—, and optionally substituted RNH—CO—, wherein R is selected from the group consisting of $C_1$-$C_6$ alkyl (e.g., methyl, ethyl, propyl, isopropyl, butyl, isobutyl, pentyl, isopentyl, or the like), wherein the substituents are selected from the group consisting of $C_1$-$C_6$ alkyl, halogen (e.g., F or Cl), CN, $N_3$, and $OR^5$;

$R^4$ is selected from the group consisting of H, OH, halogen (e.g., F), $C_1$-$C_6$ alkyl (e.g., methyl or ethyl), and $C_1$-$C_6$ alkoxy (e.g., methoxy or ethoxy); B is selected from the group consisting of:

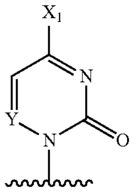

and

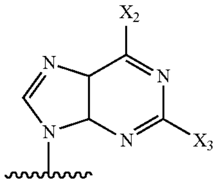

wherein $X_1$ is selected from the group consisting of —OH, —$NH_2$, $R^5CONH$—, $R^5COO$—, or $R^5O(C{=}O)NH$—;

$X_2$ is selected from the group consisting of —OH, —SH, —$NH_2$, $R^5COO$—, $R^5COS$—, $R^5CONH_2$—, or $R^5O(C{=}O)NH$—;

$X_3$ is selected from the group consisting of H, F, —OH, and —$NH_2$;

Y is selected from the group consisting of CH and N;

Z is H, —OH, or F; and $R^5$ is selected from the group consisting of H, $C_1$-$C_6$ alkyl (e.g., methyl, ethyl, propyl, or isopropyl), $C_2$-$C_6$ alkynyl (e.g., ethynyl), $C_2$-$C_6$ alkenyl (e.g., ethenyl), halo $C_1$-$C_6$ alkyl (e.g., 2-chloroethyl, 2-fluoroethyl, or trifluoroethyl), phenyl optionally substituted with $C_{1-6}$ alkyl, $C_{1-6}$ alkoxy, CN, $N_3$, OH, $NH_2$, halogen (e.g., F, Cl, Br, or I), and naphthyl optionally substituted with $C_{1-6}$ alkyl, $C_{1-6}$ alkoxy, CN, $N_3$, OH, $NH_2$, halogen (e.g., F, Cl, Br, or I).

The following compounds or pharmaceutically acceptable salts thereof are preferred:

1

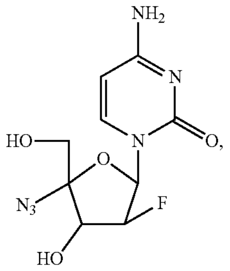

2

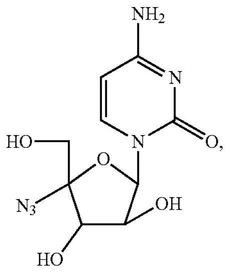

3

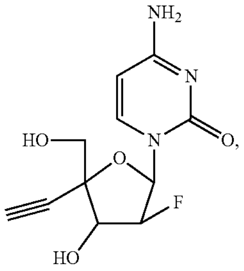

-continued

4

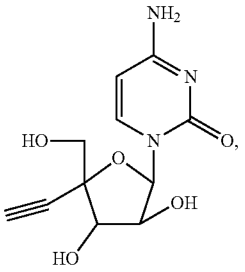

5

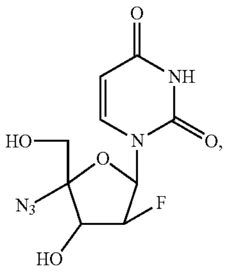

6

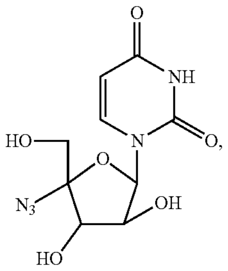

7

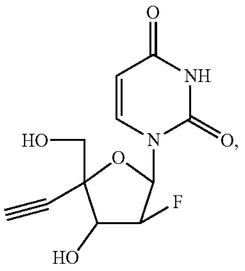

8

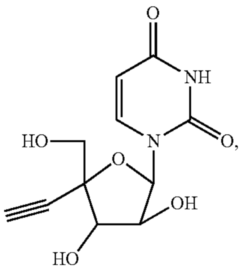

9

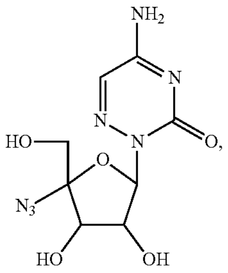

-continued
10
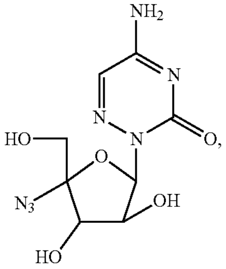
11
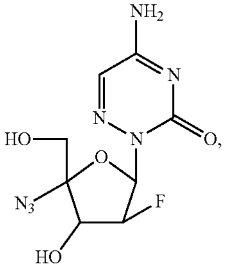
12
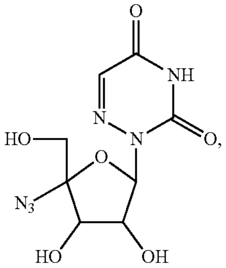
13
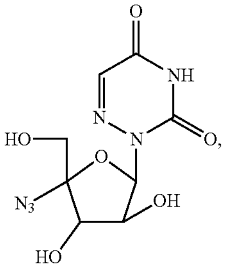
14
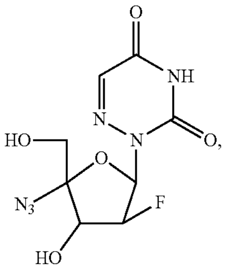
-continued
15
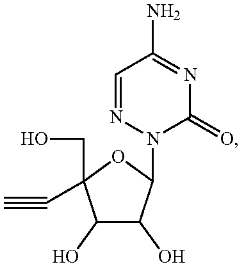
16
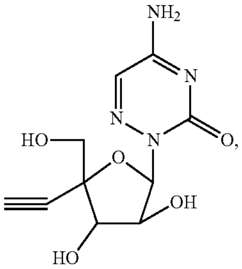
17
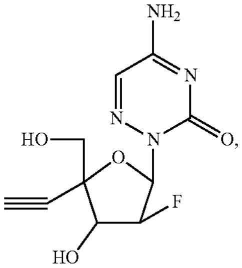
18
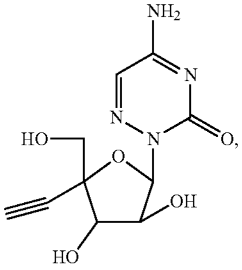
19
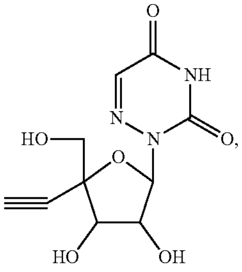

-continued

20

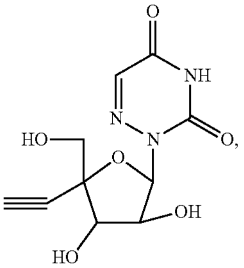

21

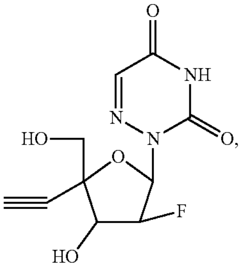

22

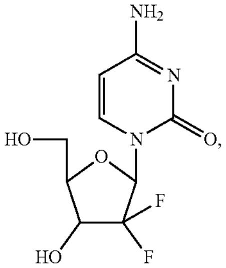

23

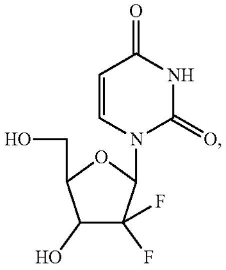

24

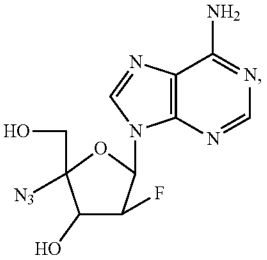

25

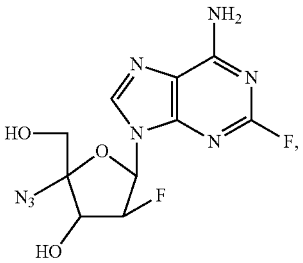

-continued

CL-236

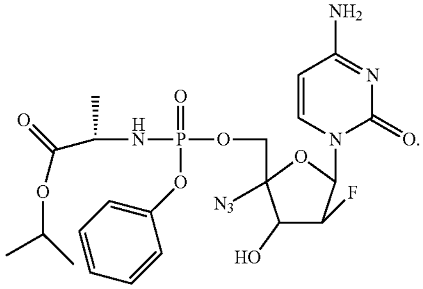

The pharmaceutically acceptable salts of the compound represented by formula (I) include, but are not limited to, for example, salts formed by the compound of formula (I) and the following acids: hydrochloric acid, hydrobromic acid, sulfamic acid, sulfuric acid, phosphoric acid, nitric acid, formic acid, acetic acid, propionic acid, oxalic acid, glycolic acid, malonic acid, benzoic acid, lactic acid, gluconic acid, citric acid, tartaric acid, succinic acid, fumaric acid, maleic acid, mandelic acid, malic acid, methanesulfonic acid, ethanesulfonic acid, 2-hydroxyethanesulfonic acid, benzenesulfonic acid, p-toluenesulfonic acid, naphthalenesulfonic acid, naphthalene disulfonic acid, camphorsulfonic acid, scorbic palmitatic acid, salicylic acid, sulfosalicylic acid, 2-hydroxy-3-naphthoic acid, phthalic acid, lysine, arginine, glutamic acid, glycine, serine, threonine, alanine, isoleucine, leucine, or the like.

The compounds represented by formula (I) may be commercially available or prepared by known methods.

The coronavirus infectious disease used herein is a disease caused by infection with a virus of Coronaviridae, including diseases caused by infected humans or other animals, in particular diseases caused by human coronaviruses that infect humans including, but not limited to, diseases caused by infection with CoV-229E, -OC43, -NL63, —HKU1, SARS-CoV, MERS-CoV, and 2019-nCoV (or known as COVID-19).

The effective amount of the compound of formula (I) for the treatment and prevention of coronavirus infectious diseases may be determined by a person skilled in the art based on the information provided herein. For example, the dosage for an adult may be 1 to 500 mg/day, optionally 1 to 50 mg/day, optionally 1 to 20 mg/day; optionally 1 to 10 mg/day, optionally 5 mg/day. It may be administered by a single dose or multiple doses.

The route of administration may be oral or parenteral administration. It may be an immediate-release dosage form, a sustained-release dosage form, or a controlled-release dosage form. The specific dosage forms may be various kinds of conventional dosage forms in the art. For instance, examples of oral preparations may include tablets, hard or soft capsules, aqueous or oily suspensions, granules, emulsions, syrups, or elixirs, and the like. Examples of injections may include injections, powder injections, and the like.

DETAILED DESCRIPTION

The specific embodiments of the present disclosure will be elaborated below. It should be appreciated that the specific embodiments described herein are merely intended to exemplarily illustrate, and not limit the present disclosure.

Test Example 1. Test for Activity of Azvudine Amine Phosphate Prodrug CL-236 Against Novel Coronavirus

(I) Experimental Materials and Reagents

1. Cell line: Huh 7 cells preserved in the inventors' laboratory;
2. Viral strain: 2019-nCoV (COVID-19);
3. Test drug: Azvudine amine phosphate prodrug (CL-236)
4. Positive control drug: Remdesivir;
5. Reagents: DMEM medium (Gibco), fetal bovine serum (Gibco), Penicillin-Streptomycin, Pancreatin, MTT (Amresco), etc.;
6. Kits: QIAamp viral RNA mini kit (52906, Qiagen) and One Step TB Green PrimeScript PLUS RT-PCR Kit (Perfect Real Time) (RR096A TaKaRa)
7. Consumables: cell culture plates, 96-well ELISA plates, etc.;
8. Instruments: multifunctional enzyme marker, StepOne-Plus fluorescence quantitative PCR, $CO_2$ incubator, etc.

(II) Experimental Steps

1. Cytotoxicity Assay of Azvudine Amine Phosphate Prodrug CL-236

Toxicity of the Azvudine amine phosphate prodrug CL-236 to Huh 7 cells was tested by MTT assay. MTT was an abbreviated form of 3-(4,5)-dimethylthiahiazo(-z-yl)-3, 5-di-phenytetrazoliumromide, which was a yellow dye. MTT colorimetric assay is a method for detecting cell survival and growth. Its detection principle was that succinate dehydrogenase in the mitochondria of viable cells enabled exogenous MTT to be reduced to water-insoluble blue-purple crystalline formazan and deposited in the cells, whereas dead cells did not have such a function. 10% SDS (dissolved in 0.01 mol/L of HCl solution) could dissolve the formazan in cells and its light absorption value was measured at a wavelength of 570 nm with a multi-purpose microplate reader, which might indirectly reflect the number of viable cells. Within a certain range of cell counts, the amount of MTT crystals formed was directly proportional to the cell counts. By measuring the light absorption values at a wavelength of 570 nm in case of different interferon concentrations, it was possible to calculate the survival rate of the cells at this drug concentration and then calculate the concentration cytotoxicity 50% (CC50) of the drug.

Huh 7 cells were inoculated one day ahead in a 96-well plate, with 1×104 cells for each well (note that the most marginal wells of the 96-well plate did not serve as experimental wells and PBS was added to prevent volatilization of media in other wells). The cells' states were observed, and upon reaching about 50%, the Azvudine amine phosphate prodrug CL-236 was subjected to 2-fold dilution with a DMEM medium containing 2% FBS, and then added to the cell plate at 100 μL/well. Six replicates were set for each concentration. At the same time, a control group (drug-free group) and a blank group were set (cell-free group). The cell plate was incubated in a 5% CO2 incubator at 37° C. At 48 h post dosing, 25 μL of MTT solutions (5 mg/mL) were added to each well. After 4 h continued incubation, 125 μL of 10% SDS (dissolved in 0.01 mol/L of HCl solution) were added to each well, and the cells were gently pipetted and left for 2 h to allow the crystals to completely dissolve. The blank group was zeroed. The OD570 was measured. The survival rate was calculated based on the following equation: survival rate (%)=OD570 for dosing group/OD570 for control group×100%. At the same time, the concentration cytotoxicity 50% (CC50) of the drug was calculated.

2. Evaluation on Inhibitory Effect of Azvudine Amine Phosphate Prodrug CL-236 Against 2019-nCoV (COVID-19) Viruses The antiviral activity assay was performed on a Huh 7 cell model. Three replicate wells were set for each assay and the assay was repeated three times in total.

1) In each well of a 24-well cell culture plate, 5×104 Huh 7 cells were inoculated. Under the culture conditions of 37° C. and 5% CO2, when the confluence reached 60%, 200 μL of 2019-nCoV (COVID-19) virus solution diluted with a DMEM medium containing 2% FBS were added to each well respectively according to the multiplicity of infection MOI of 0.005. After adsorption for 1 h in a 5% CO2 incubator at 37° C., the virus solution was discarded. The positive control drug and the Azvudine amine phosphate prodrug CL-236 were subjected to 2-fold dilution with a DMEM medium containing 2% FBS from the maximum non-toxic concentration, and added to the cell plate at 500 μL/well. Meanwhile, a control group (drug-free group) was set and the supernatant virus solution was collected at 48 h after infection.

2) RNA quantification of collected viruses by real-time RT-PCR (qRT-PCR):

From the collected supernatant virus solutions, 140 μL were measured separately, and subjected to RNA extraction according to the instruction of the QIAamp viral RNA mini kit. The qRT-PCR detection was carried out using the One Step TB Green PrimeScript PLUS RT-PCR Kit (Perfect Real Time), and the primers were RBD-qF1: 5'-CAATGGTT-TAACAGGCACAGG-3' (SEQ. ID. NO. 1); and RBD-qR1: 5'-CTCAAGTGTCTGTGGATCACG-3'(SEQ. ID. NO. 2).

The total volume of the reaction system was 20 μL:10 μL of 2× One Step TB Green RT-PCR Buffer 4, 1.2 μL of TaKaRa Ex Taq HS Mix, 0.4 μL of PrimeScript PLUS RTase Mix, 0.8 μL each of RBD-qF1 and RBD-qR1, 0.4 μL of ROX Reference Dye (50×), 2 μL of viral RNA, and 4.4 μL of RNase Free dH2O. The reaction parameters were as follows: reverse transcription at 42° C. for 5 min, pre-denaturation at 95° C. for 10 s, PCR for 40 cycles including denaturation at 95° C. for 10 s and annealing and extension at 60° C. for 30 s.

3) The inhibition rates of the drug at the concentrations were calculated. Inhibition rate (%)=1−viral RNA copies in experimental group/viral RNA copies in drug-free group× 100%. At the same time, the median effective concentration (EC50) and therapeutic index (TI) of the drug were calculated, therapeutic index (TI)=concentration cytotoxicity 50% (CC50)/median effective concentration (EC50).

(III) Calculation of Experimental Results

TABLE 1

Inhibitory effect of Azvudine amine phosphate prodrug CL-236 against COVID-19 activity

| Test Drugs | Concentration (uM) | Virus Inhibition Rate (%) | $EC_{50}$ | $CC_{50}$ | SI |
|---|---|---|---|---|---|
| CL-236 | 0.1 | 9.38 | 3.20 uM | 66.15 uM | 20.7 |
| | 0.4 | 18.75 | | | |
| | 1.6 | 37.50 | | | |
| | 6.4 | 65.63 | | | |

TABLE 1-continued

| Inhibitory effect of Azvudine amine phosphate prodrug CL-236 against COVID-19 activity | | | | | |
|---|---|---|---|---|---|
| Test Drugs | Concentration (uM) | Virus Inhibition Rate (%) | $EC_{50}$ | $CC_{50}$ | SI |
| | 25.6 | 75.00 | | | |
| | 102.4 | 81.25 | | | |
| Remdesivir | | | 1.50 uM | >45.0 uM | >30.0 |

Test Example 2

Clinical trials validated the efficacy and safety of Compound 1 for the treatment of novel coronavirus (COVID-19) pneumonia.

Twenty patients diagnosed with novel coronavirus infection by the nucleic acid test were selected and divided into the Azvudine (Compound 1) group and the Kaletra control group, 10 cases for each group. The Azvudine group followed the following therapeutic regime: 5 mg daily (oral administration, 5 tablets, 1 mg for each tablet). The Kaletra control group followed the following therapeutic regime: Kaletra (oral administration, 2 tablets/day, 250 mg/tablet)+ arbidol (oral administration 200 mg/time, 3 times/day)+ interferon (5 million U, twice daily by aerosol inhalation). The nucleic acid changes and body temperature changes were measured, and various symptoms were observed.

The results were as shown in the table below.

| Patient No. | Kaletra Control Group From inclusion confirmed by nucleic acid test to clearance/discharge | Azvudine Group From inclusion confirmed by nucleic acid test to clearance/discharge |
|---|---|---|
| Patient 1 | Clearance: day 6, continuing the treatment | |
| Patient 2 | Clearance: day 3<br>Discharge: day 5 | |
| Patient 3 | Clearance: day 4<br>Discharge: day 7 | |
| Patient 4 | Being treated at day 7 | |
| Patient 5 | Being treated at day 6 | |
| Patient 6 | Clearance: day 4 | |
| Patient 7 | Clearance: day 2<br>Discharge: day 5 | |
| Patient 8 | Being treated at day 6 | |
| Patient 9 | Being treated at day 5 | |
| Patient 10 | Clearance: day 3 | |
| Patient 11 | | Clearance: day 4<br>Discharge: day 7 |
| Patient 12 | | Clearance: day 4<br>Discharge: day 6 |
| Patient 13 | | Clearance: day 4<br>Discharge: day 6 |
| Patient 14 | | Clearance: day 4<br>Discharge: day 8 |
| Patient 15 | | Clearance: day 2<br>Discharge: day 7 |
| Patient 16 | | Clearance after one week |
| Patient 17 | | Clearance after one week |
| Patient 18 | | Clearance: day 3<br>Discharge: day 6 |
| Patient 19 | | Clearance: day 2<br>Discharge: day 5 |
| Patient 20 | | Clearance: day 3 |

The results of the clinical trials suggested that all of the 10 patients with novel coronavirus infection in the Azvudine group turned negative by the nucleic acid test, and seven of them were discharged within 8 days.

The above results of the clinical trials suggested that treatment of novel coronavirus pneumonia with Compound 1 showed significant clinical therapeutic advantages in several indicators, i.e., patients' nucleic acid clearance rate, course of clearance, cure rate, and course of cure.

One of the patients, who had failed to turn negative after supportive treatment with Kaletra for more than 20 days, turned negative three days after treatment with Compound 1. During the treatment, no drug-related toxic and side effects were found.

In the in vitro test system, Azvudine could not be effectively activated through phosphate esterification, so the Azvudine amine phosphate prodrug (CL-236) was used to measure its activity against novel coronavirus indirectly. The trials of AIDS treated with Azvudine have told that Azvudine could be effectively activated in human bodies. Therefore, in human clinical trials, Azvudine instead of Azvudine amine phosphate prodrug was used directly to treat the novel coronavirus pneumonia.

The invention claimed is:

1. A method for treating a coronavirus infectious disease, comprising administering to a patient in need thereof a therapeutically or prophylactically effective amount of a compound represented by formula (I) or pharmaceutically acceptable salts thereof, (I)

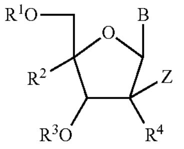

wherein in the formula (I), $R^1$ is H, $R^5$—CO—, or

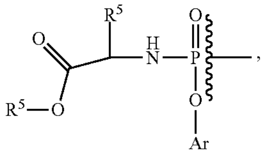

wherein Ar is phenyl, substituted phenyl, naphthyl, or substituted naphthyl, wherein the substituents are selected from the group consisting of $C_{1-6}$ alkyl, F, Cl, Br, I, CN, $N_3$, OH, $NH_2$, $OR^5$, and $NHR^5$;

$R^2$ is H, azido, $C_1$-$C_6$ alkyl, $C_1$-$C_6$ alkoxy, $C_2$-$C_6$ alkynyl, $C_2$-$C_6$ alkenyl, or halo $C_1$-$C_6$ alkyl;

$R^3$ is H, unsubstituted or substituted R—CO—, unsubstituted or substituted R—O(C═O)—, or unsubstituted or substituted RNH—CO—, wherein R is $C_1$-$C_6$ alkyl, wherein the substituents are selected from the group consisting of F Cl CN, $N_3$, and $OR^5$;

$R^4$ is H, OH, halogen, $C_1$-$C_6$ alkyl, or $C_1$-$C_6$ alkoxy;

B is selected from the group consisting of:

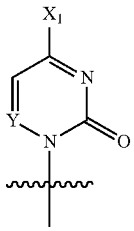

and

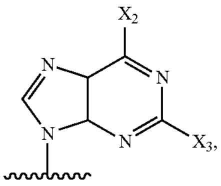

wherein $X_1$ is —OH, —$NH_2$, $R^5$CONH—, $R^5$COO—, or $R^5$O(C═O) NH—;

$X_2$ is OH, SH, $NH_2$, $R^5$COO—, $R^5$COS—, $R^5CONH_2$—, or $R^5$O(C═O) NH—;

$X_3$ is H, F, OH, or $NH_2$;

Y is CH or N;

Z is H, OH, or F; and $R^5$ is selected from the group consisting of H, $C_1$-$C_6$ alkyl, $C_2$-$C_6$ alkynyl, $C_2$-$C_6$ alkenyl, halo $C_1$-$C_6$ alkyl, phenyl, phenyl substituted with $C_{1-6}$ alkyl, $C_{1-6}$ alkoxy, CN, $N_3$, OH, $NH_2$, F, Cl, Br, I, and naphthyl substituted with $C_{1-6}$ alkyl, $C_{1-6}$ alkoxy, CN, $N_3$, OH, $NH_2$, or halogen;

wherein the coronavirus infectious disease is a disease caused by infection with a virus of COVID-19.

2. The method for treating a coronavirus infectious disease according to claim 1, wherein $R^2$ is H, azido, methyl, ethyl, methoxy, ethoxy, ethynyl, ethenyl, 2-chloroethyl, 2-fluoroethyl, or trifluoroethyl.

3. The method for treating a coronavirus infectious disease according to claim 1, wherein R is methyl, ethyl, propyl, isopropyl, butyl, isobutyl, pentyl, or isopentyl.

4. The method for treating a coronavirus infectious disease according to claim 1, wherein $R^4$ is H, OH, F, methyl ethyl, methoxy, or ethoxy.

5. The method for treating a coronavirus infectious disease according to claim 1, wherein $R^5$ is selected from the group consisting of H, methyl, ethyl, propyl, isopropyl, ethynyl, ethenyl, 2-chloroethyl, 2-fluoroethyl, trifluoroethyl, phenyl, phenyl substituted with $C_{1-6}$ alkyl, $C_{1-6}$ alkoxy, CN, $N_3$, OH, $NH_2$, F, Cl, Br, or I, naphthyl, or naphthyl substituted with $C_{1-6}$ alkyl, $C_{1-6}$ alkoxy, CN, $N_3$, OH, $NH_2$, F, Cl, Br, or I.

6. The method for treating a coronavirus infectious disease according to claim 1, wherein the compound represented by formula (I) is the following compound:

1

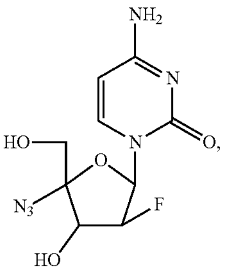

2

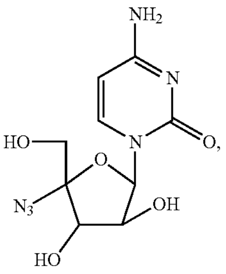

-continued
3
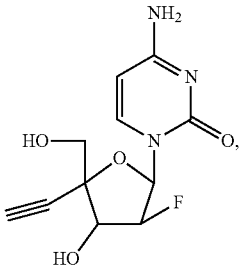
4
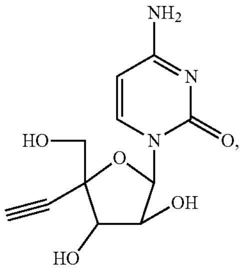
5
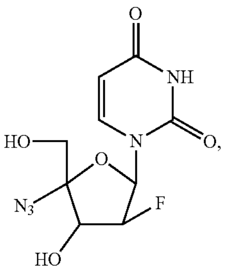
6
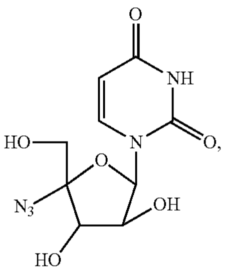
7
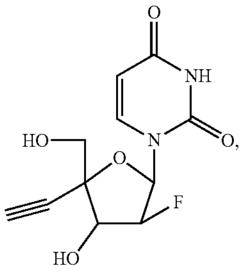
8
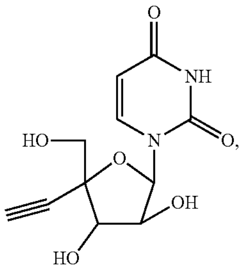
-continued
9
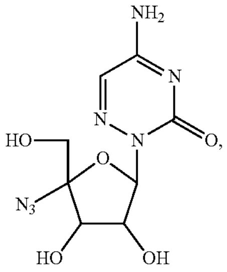
10
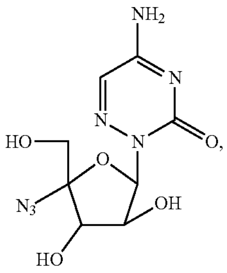
11
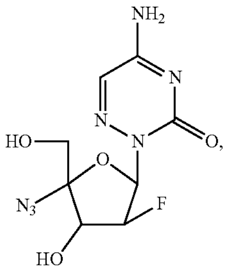
12
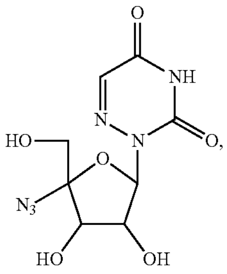
13
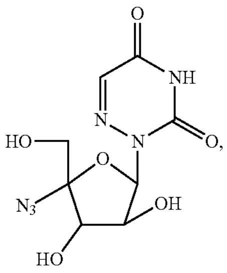

-continued
14
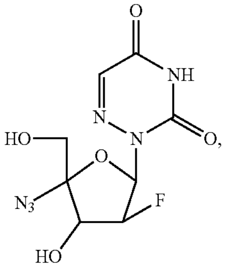
15
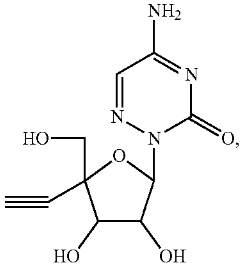
16
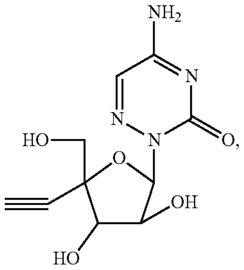
17
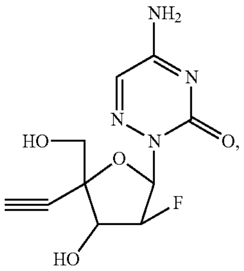
18
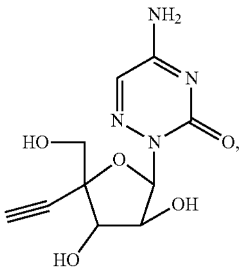
19
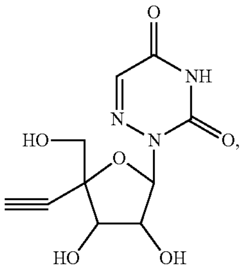
-continued
20
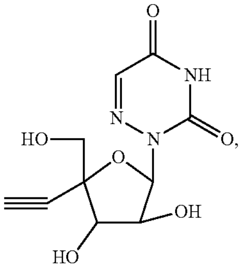
21
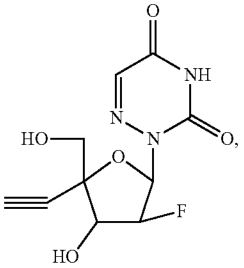
22
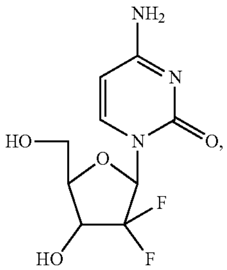
23
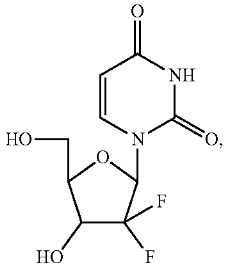
24
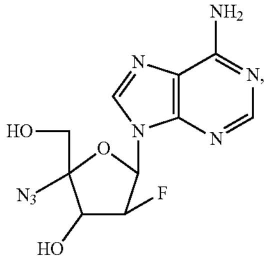
or
25
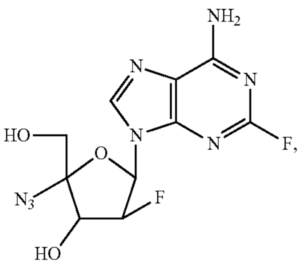
or -continued

CL-236

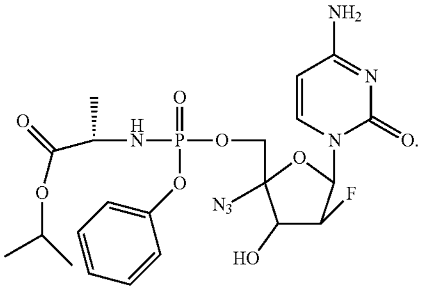

7. The method for treating a coronavirus infectious disease according to claim 1, wherein the pharmaceutically acceptable salts of the compound represented by formula (I) are salts formed by the compound of formula (I) and the following acids: hydrochloric acid, hydrobromic acid, sulfamic acid, sulfuric acid, phosphoric acid, nitric acid, formic acid, acetic acid, propionic acid, oxalic acid, glycolic acid, malonic acid, benzoic acid, lactic acid, gluconic acid, citric acid, tartaric acid, succinic acid, fumaric acid, maleic acid, mandelic acid, malic acid, methanesulfonic acid, ethanesulfonic acid, 2-hydroxyethanesulfonic acid, benzenesulfonic acid, p-toluenesulfonic acid, naphthalenesulfonic acid, naphthalene disulfonic acid, camphorsulfonic acid, scorbic palmitatic acid, salicylic acid, sulfosalicylic acid, 2-hydroxy-3-naphthoic acid, phthalic acid, lysine, arginine, glutamic acid, glycine, serine, threonine, alanine, isoleucine, or leucine.

8. The method for treating a coronavirus infectious disease according to claim 1, wherein the coronavirus infectious disease is a disease caused by infected humans or other animals.

9. The method for treating a coronavirus infectious disease according to claim 1, wherein the compound represented by formula (I) or the pharmaceutically acceptable salts thereof is provided in a dosage form selected from the group consisting of an immediate-release dosage form, a sustained-release dosage form, or a controlled-release dosage form.

10. The method for treating a coronavirus infectious disease according to claim 9, wherein the dosage form is a tablet, a hard or soft capsule, an aqueous or oily suspension, a granule, an emulsion, a syrup, an elixir, an injection, or a powder injection.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthesized

<400> SEQUENCE: 1

caatggttta acaggcacag g                                              21


<210> SEQ ID NO 2
<211> LENGTH: 21
<212> TYPE: DNA
<213> ORGANISM: Artificial Sequence
<220> FEATURE:
```

-continued

```
<223> OTHER INFORMATION: Synthesized

<400> SEQUENCE: 2

ctcaagtgtc tgtggatcac g                                              21
```